(12) United States Patent
Meier et al.

(10) Patent No.: US 6,212,488 B1
(45) Date of Patent: Apr. 3, 2001

(54) RISER REACTOR SIMULATION IN CATALYTIC CRACKING

(75) Inventors: Paul F. Meier; Dhananjay B. Ghonasgi, both of Bartlesville, OK (US); Michael David Wardinsky, Lake Jackson, TX (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/119,194

(22) Filed: Jul. 20, 1998

(51) Int. Cl.$^7$ .................. G06G 7/48; G06G 7/58
(52) U.S. Cl. ........................ 703/12; 703/2; 703/6
(58) Field of Search ........................ 703/2, 6, 12

(56) References Cited

U.S. PATENT DOCUMENTS

| | | |
|---|---|---|
| 4,187,548 | 2/1980 | Gross et al. .................. 364/578 |
| 4,243,630 | 1/1981 | Kliesch et al. .................. 422/62 |
| 5,699,270 | 12/1997 | Ashe et al. .................. 364/500 |
| 5,774,381 * | 6/1998 | Meier .................. 364/578 |

* cited by examiner

Primary Examiner—Kevin J. Teska
Assistant Examiner—William Thomson
(74) Attorney, Agent, or Firm—Jeffrey R. Anderson (57) ABSTRACT

A predictive kinetic model is disclosed for simulating fluid catalytic cracking of large hydrocarbon molecules having a lumping scheme that includes hydrocarbon descriptions based on boiling point distribution and chemical properties. The simulation results in a nearly continuous prediction of products as function of boiling point temperature. The lumping scheme defines a relatively large number of small fixed boiling-point range pseudo-components for describing product material, and a smaller number of larger boiling-point range pseudo-components for describing feed conversion and selectivity. The chemical properties for describing hydrocarbons include total hydrogen, aromatic carbon and aromatic hydrogen.

21 Claims, 6 Drawing Sheets

RISER REACTOR SIMULATION IN CATALYTIC CRACKING

This invention relates to operations performed in a digital computer, and more specifically to a computer software program for simulating a chemical reaction involving breaking down of large molecules of hydrocarbons into smaller, lighter, more valuable molecules.

BACKGROUND OF THE INVENTION

The most important hydrocarbon refining process, which in the 1940's revolutionized the refining industry, is catalytic cracking of large hydrocarbon molecules. The catalytic cracking process is the largest catalytic process in the world, and is extensively used today for the production of gasoline from high boiling hydrocarbons such as residual and gas oil fractions. In many refineries heavy residual oil resulting from distillation of crude oil, or so called topped crude or simply resid, is pretreated in a hydrotreating process before sending the resid to a fluid catalytic cracking (FCC) process step. As used herein a "heavy oil" is taken to mean a hydrocarbon liquid boiling at atmospheric pressure in a range of from about 650° F. to as high as 1500° F., and which contains a variety of very complex chemical compounds.

A principal factor which affects the economic viability of a fluidic catalytic cracking unit is the amount of the feedstock that is converted to a desired product such as gasoline. In many refineries the feed to an FCC unit consists of a heavy oil containing an unlimited mixture of complex molecules of straight and branched paraffins, cycloparaffins, and aromatics ranging from monoaromatics to four or five rings with a vast variety of side chains. It is generally very difficult to maintain a desired conversion of this heavy oil feedstock in an FCC unit.

In recent years the use of computers has increased greatly as a means to examine complex chemical reactions by simulation techniques. Digital computer simulation of catalytic cracking reactions is particularly valuable in many areas relating to refining of heavy oil such as predicting what a cracking reaction will yield under different operating conditions, in optimizing operation of a riser reactor, in planning and scheduling operations, and perhaps most importantly in selecting optimum crude and catalyst purchases.

An effective kinetic model to describe riser reactor cracking of hydrocarbon oils includes two essential features: First is a reasonable physical description of the riser reactor dynamics, accounting for variations in temperature, space velocity, residence time, cracking rates and catalyst deactivation over a wide range of feed stock composition and process conditions. Second is reliable predictions of the variation of the rate constants for cracking and product selectivity as a function of oil and catalyst properties.

A highly effective method and apparatus for simulating a catalytic cracking reaction by relating conversion, selectivity, and product yields to feedstock properties is disclosed and claimed in U.S. Pat. No. 5, 774,381 issued Jun. 30, 1998, to Paul F. Meier. However, the method disclosed in that patent relates hydrocarbon conversion to process variables and to feedstock properties that are routinely measured at the refinery such as API gravity, measured impurities (sulfur, Ni, and V), basic nitrogen, carbon residue and viscosity. While the disclosure of this patent is regarded as representing a significant contribution to the simulation art in predicting conversion of heavy hydrocarbons to cracked products, it is insufficient to differentiate chemical differences between crude feed types, i.e., sweet or sour, or between pretreatment, i.e., virgin or hydrotreated, or between fresh or recycle streams. Accordingly, it would be highly desirable to have a kinetic model for a riser reactor in catalytic cracking that is independent of the feed source or pretreatment.

An object of this invention is to improve efficiency of commercial refining operations.

A more specific object is to predict how well a specific oil fraction would run in a riser reactor of an FCC Unit.

Another object of this invention is to obtain data that facilitates improved selection of catalyst and/or crude oil stocks purchased for processing in a refinery.

Yet another object is to obtain kinetic reaction data that can be integrated into a process model for optimized operation of a total FCC process.

Still, another object of this invention is to make the kinetic model independent of the feed source and pretreatment.

Another more specific object of this invention is to predict essentially continuous boiling point distribution curves of $C_5$ cracked hydrocarbon products.

SUMMARY OF THE INVENTION

According to this invention, the foregoing and other objects and advantages are attained in a computer implemented method for mathematical modeling of reactions associated with catalytic cracking of residual and gas oil feedstocks to lower molecular weight products as a result of contacting with catalyst in a riser reactor of an FCC unit. The computer program simulating this reaction relies on the kinetic model for the riser reactor cracking of residual and gas oil feeds. A lumping scheme for the kinetic model according to this invention incorporates a relatively large number of small fixed boiling-point range pseudo-components, referred to herein as product lumps, for describing product material. A smaller number of larger boiling-point range pseudo-components, referred to herein as basic lumps, are defined for describing feed conversion and selectivity. A reaction conversion network flowing from heavier to lighter components is defined for the basic lumps, and an equation which can be generalized to any number of pseudo-components predicts changes in concentration for both the basic and product lumps as the simulated reaction proceeds.

In a preferred embodiment of this invention, the lumping scheme defines thirty-four pseudo-components for the product lumps covering an overall boiling point temperature range beginning at about 40° F. and extending to about 1500° F. Preferably five pseudo-components are defined for basic lumps covering the same overall boiling point temperature range. Each of the pseudo-components are treated as pure components for constructing kinetic conversion equations. Pure component characteristics are used for describing compounds up to and including $C_4$ hydrocarbons. The description of the hydrocarbons for the kinetic model is preferably based on measurements that yield chemical analysis in terms of total hydrogen, aromatic carbon, and aromatic hydrogen present in the feed. Conversion reactions are considered to be first order, and the kinetic model includes: rate constants for individual pseudo-components that are experimentally determined as functions of oil and catalyst properties, temperature, and reactor configuration; activation energies that are determined using linear interpolation and extrapolation between known values of activation energies for gas-oil and gasoline; and a second order decay function to account for catalyst deactivation. The computer simulation sequentially calculates the reaction rate constants at riser temperature, the fractional conversion and selectivity of the feed, distribution of product lumps included in the basic lumps, and yields of lower molecular weight products. The results of the simulated reaction, which include hydrocarbon conversions achieved, and yields of cracked products can be presented as printed numerical outputs, or presented as computer generated graphic displays. Accordingly, the kinetic model in this invention allows prediction of a nearly continuous distribution of products in terms of boiling-point.

In another aspect, apparatus according to this invention includes a programmable computer for storing the kinetic model for simulating the riser reactor cracking reaction, along with the required input data including process conditions for the reaction to be simulated, such as: oil properties of the fresh feed, recycle throughput ratio, equilibrium catalyst properties, space velocity, catalyst residence time and reactor temperature.

In accordance with yet another aspect of this invention, a program storage device comprises a computer readable medium having computer program code means embodied therein for causing the computer to carry out the above described method.

Still other objects and advantages of the present invention will become readily apparent to those skilled in the art from the following detailed description and the drawings, wherein there is shown and described only the preferred embodiments of this invention.

DETAILED DESCRIPTION OF THE PREFERRED EMBODIMENT

Figure 1:
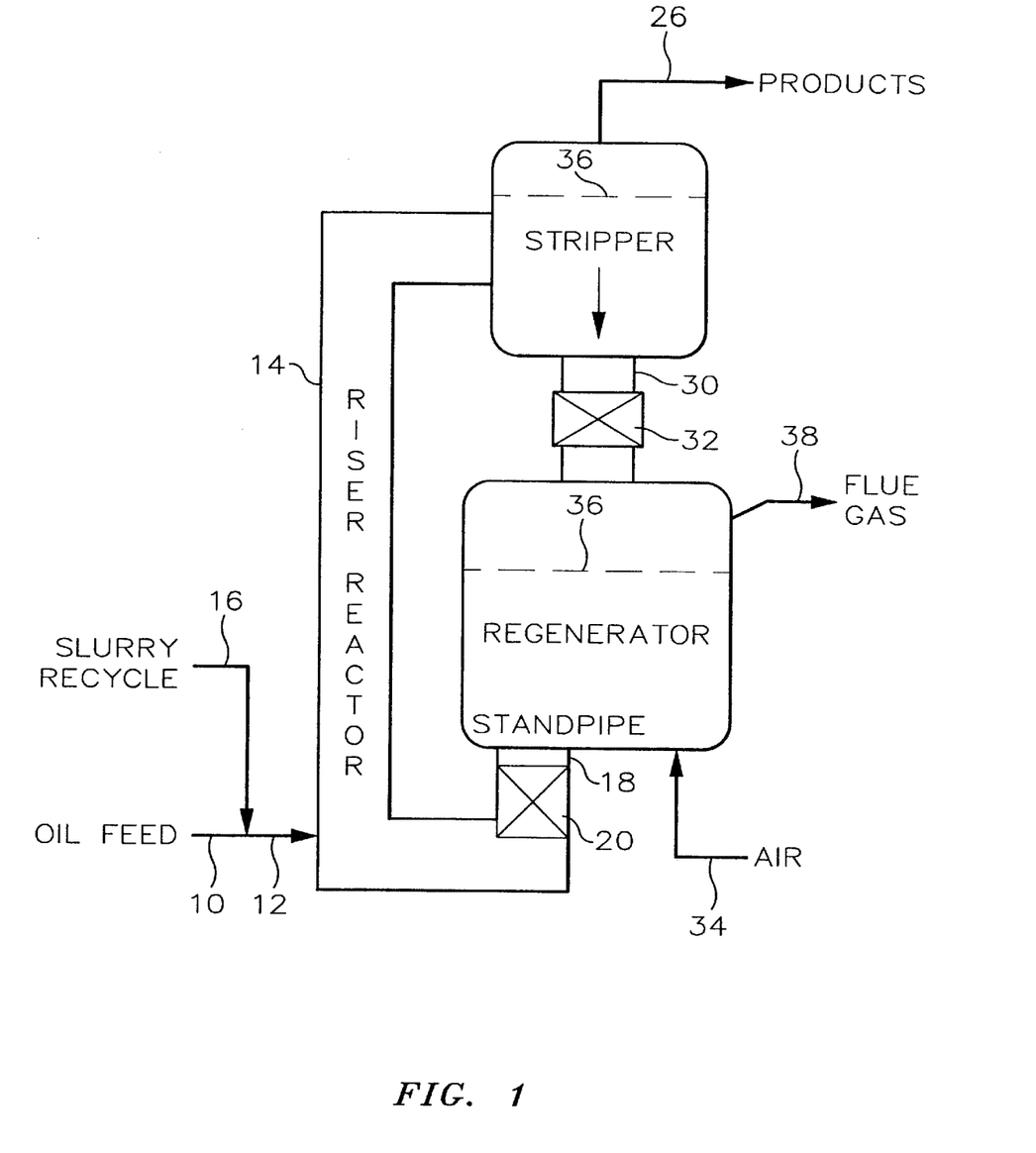
FIG. 1 is a schematic illustration of the catalyst section of a stacked configuration of a typical FCC unit employing a riser reactor.

Fluidized catalytic cracking processes employ catalyst in the form of very fine particles which behave as fluids when aerated with a vapor. Since the cracking process produces coke which remains on the catalyst particles and rapidly lowers its activity, the fluidized catalyst is circulated continuously between a reaction zone and a regeneration zone. In addition to facilitating regeneration of the catalyst, the catalyst circulation acts as a vehicle to transfer heat from the regenerator to the oil feed. A basic fluidized reactor configuration is a stacked arrangement as shown in FIG. 1. In this configuration, the reaction occurs in a riser reactor with control of the reaction being maintained by varying the catalyst circulation rate.

Referring now to the drawings and in particular to FIG. 1, which illustrates the catalyst circulation section of an FCC unit, a heavy oil feed is supplied through the combination of conduits 10 and 12 to the riser reactor 14. The reactor feed can include a slurry recycle oil stream from a fractionator (not shown) associated with the catalyst circulation section via conduit 16. A zeolite cracking catalyst is generally preferred, but any suitable cracking catalyst may be utilized. Heated regenerated catalyst from a standpipe 18, having a slide valve 20, is combined with the feed oil in the riser reactor 14 such that a catalyst/hydrocarbon mixture rises in reactor 14, where the major portion of the cracking reaction occurs in the presence of freshly regenerated catalyst and at suitable temperatures, the catalyst/hydrocarbon mixture is passed from the riser reactor 14 to a stripper 22 where fine catalyst particles are separated from the hydrocarbon vapor. In the stripper 22, there may be further contact between hydrocarbon vapor and active cracking catalyst within a relatively dense catalyst bed illustrated below the dash line 24. The reaction products are withdrawn overhead from stripper 22 via conduit 26 and transferred to a product recovery section which includes at least one fractionator (not shown).

A stream of spent or coked catalyst is continuously passed from stripper 22 to a regenerator 28 via transfer conduit 30 having a slide valve 32. Carbon is burned off the spent catalyst in regenerator 28 in the presence of air introduced to the regenerator via conduit 34 to produce a fresh catalyst which is combined with the hydrocarbon feed. In the lower portion of regenerator 28, a relatively dense fluidized bed represented as below dash line 36 provides for contact between the catalyst particles and the oxidizing air stream supplied via conduit 34. Hot flue gas is removed from the regenerator 28 via conduit 38 for heat recovery or other suitable use (not illustrated). Average reactor temperatures are in a range of about 950° F. to 1000° F. with feed oil temperature from about 150° F. to about 500° F. and regenerator exit temperature for catalyst from about 1250° F. to about 1320° F.

Pseudo Component Description

Figure 2:
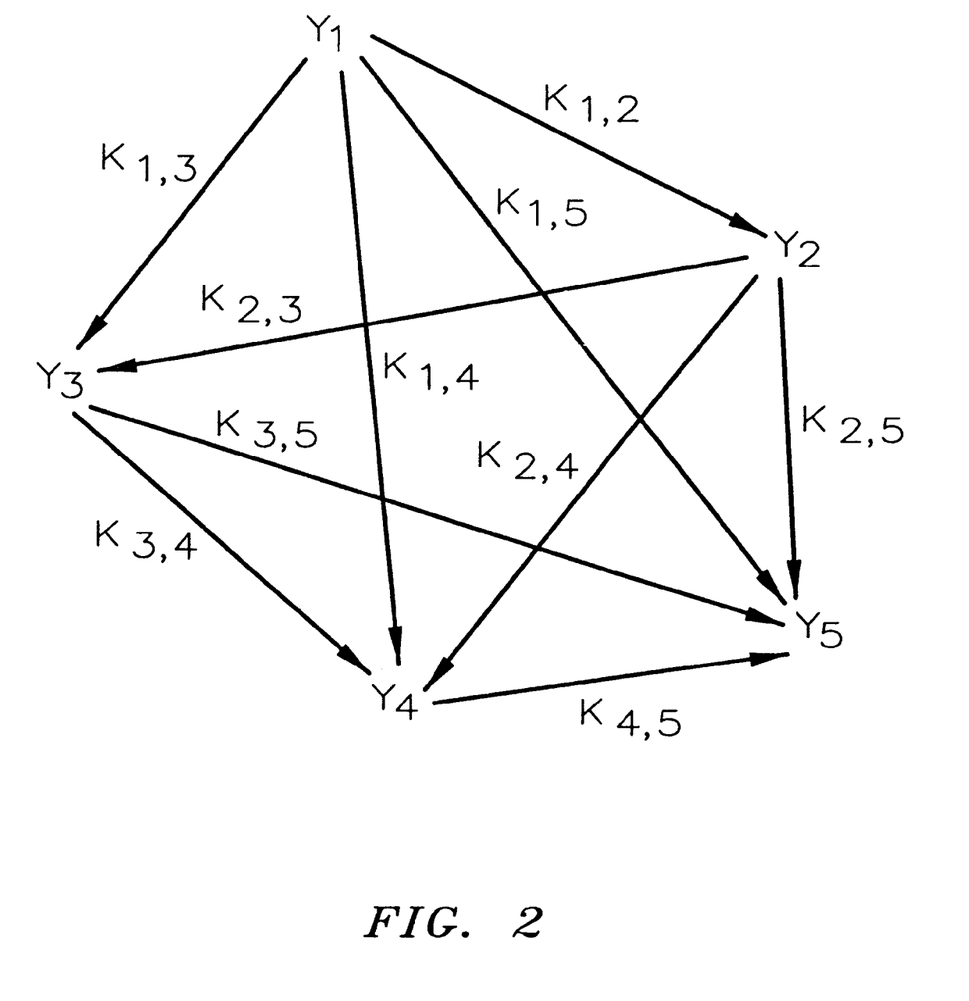
FIG. 2 illustrates the reaction paths of the chemical kinetics for a five-lump reaction conversion and selectivity scheme.

In accordance with one aspect of this invention, a mathematical kinetic model predicts conversion and selectivity of heavy oil and gas oil feeds, and yields of cracked hydrocarbon products for an FCC operation such as shown in FIG. 1. The kinetic model is based on a network of simultaneous and consecutive reaction of lumped hydrocarbon components as illustrated in FIG. 2. As used herein, a lump is a selected hydrocarbon boiling point range or a selected species in the reaction network, which can be represented by a kinetic expression. The lumping scheme groups kinetically similar molecules or components for describing an overall conversion in a simplified reaction network, which is adequate to predict the major process yields in the cracking of different charge stocks under a range of process conditions.

The preferred number and temperature increments of fixed small boiling range pseudo-components for product description is shown in Table 1 below.

TABLE I

| Pseudo - Component Increments | | |
|---|---|---|
| TBP Range | Number of Components | Increments, ° F. |
| $C_5+$ to 800° F. | 28 | 25 |
| $800+$° F. | 6 | 50 |

As previously mentioned the term pseudo-component in this context is taken to mean that the properties of material in its fixed boiling range are treated in a simulated reaction as a single pure component. Accordingly, rate constants for disappearance of reactants, product selectivity, as well as the Arrhenius temperature dependencies are identified for all compounds included in the fixed boiling range of the pseudo-component. According to this invention the first pseudo-component begins with $C_5$ compounds.

Table II below shows the upper and lower temperature for each range, as well as the average boiling-point for each small range pseudo-component. Preferred activation energies used for simulated cracking of the pseudo-components are also given in Table II. The use of thirty-four pseudo-components represents a practical compromise in the development of the riser kinetic model. For example, the highest boiling pseudo-component, number 34, can crack and form products in the form of pseudo-components numbered 1 thru 33, as well as the light gases and coke.

TABLE II

Temperatures and Energies of Small Range Pseudo-Components

| Pseudo-Component | Lower Temp. of Range (° F.) | Upper Temp. of Range (° F.) | Average Temp. of Range (° F.) | Activation Energies (BTU/lb - mole - R) |
| --- | --- | --- | --- | --- |
| 1 | 40 | 100 | 71 | 37,271 |
| 2 | 100 | 125 | 113 | 35,985 |
| 3 | 125 | 150 | 138 | 35,219 |
| 4 | 150 | 175 | 163 | 34,453 |
| 5 | 175 | 200 | 188 | 33,717 |
| 6 | 200 | 225 | 213 | 32,951 |
| 7 | 225 | 250 | 238 | 32,186 |
| 8 | 250 | 275 | 263 | 31,420 |
| 9 | 275 | 300 | 288 | 30,654 |
| 10 | 300 | 325 | 313 | 29,857 |
| 11 | 325 | 350 | 338 | 29,122 |
| 12 | 350 | 375 | 363 | 28,356 |
| 13 | 375 | 400 | 388 | 27,590 |
| 14 | 400 | 425 | 413 | 26,793 |
| 15 | 425 | 450 | 438 | 26,027 |
| 16 | 450 | 475 | 463 | 25,261 |
| 17 | 475 | 500 | 488 | 24,495 |
| 18 | 500 | 525 | 513 | 23,729 |
| 19 | 525 | 550 | 538 | 22,963 |
| 20 | 550 | 575 | 563 | 22,197 |
| 21 | 575 | 600 | 588 | 21,431 |
| 22 | 600 | 625 | 613 | 20,666 |
| 23 | 625 | 650 | 638 | 19,900 |
| 24 | 650 | 675 | 663 | 19,134 |
| 25 | 675 | 700 | 688 | 18,368 |
| 26 | 700 | 725 | 713 | 17,602 |
| 27 | 725 | 750 | 738 | 16,836 |
| 28 | 750 | 775 | 763 | 16,070 |
| 29 | 775 | 806.5 | 788 | 15,304 |
| 30 | 806.5 | 850 | 828 | 14,170 |
| 31 | 850 | 900 | 875 | 12,638 |
| 32 | 900 | 950 | 925 | 11,106 |
| 33 | 950 | 1000 | 975 | 9574 |
| 34 | 1000 | 1300 | 1025 | 8043 |

Including the thirty-four pseudo-components plus the light gases and coke, and assuming that the light gases and coke do not undergo cracking, 765 selectives are possible. Further, for each reaction the rate of disappearance and the selectivity for specific products will have a particular oil and catalyst dependence. Since such a large number of equations cannot be practically solved in a computer, a simplified pseudo-component approach, which drops calculations that contributes little to the answer, includes use of four broad boiling range lumps for conversion and selectivity calculations. Disappearance rates, however, are calculated according to the thirty-four smaller boiling range pseudo-components, thus allowing differentation of products from the broader boiling range lumps into the smaller temperature ranges. The broader lumps, which nominally represent gasoline, distillate, gas oil and resid boiling range components, are listed with their respective activation energies in Table III below.

TABLE III

Temperatures and Energies of Broad Range Pseudo-Components

| Broad Range Pseudo-Component | Temperature Range of Lump (° F.) | Activation Energies (BTU/lb-mole-R) | Small Range Pseudo-Components included in range |
| --- | --- | --- | --- |
| $y_1$ | 950+ | 8800 | 33–34 |
| $y_2$ | 625–950 | 16,070 | 23–32 |
| $y_3$ | 375–625 | 24,115 | 13–22 |
| $y_4$ | 40–375 | 32,186 | 1–12 |

Product Yield Model

Referring now to FIG. 2, there is illustrated the preferred reaction network for modeling heavy oil and gas oil cracking and the reaction rate symbols assigned to the various steps. Since these reaction rates decay rapidly during the cracking reactions in the riser reactor, it is necessary to integrate catalyst decay with the reaction kinetics to achieve a satisfactory model. Further, in accordance with this invention, each reaction rate is expressed as a function of the feed, and catalyst properties, reaction temperature and reactor configuration. Still further, with reaction rates dependent on catalyst properties, a straight forward method exists for representing effects of changing riser temperature using an Arrhenius type approach, as will be more fully illustrated hereinafter.

The reaction scheme illustrated in FIG. 2 uses the broad temperature range pseudo component $y_1$, $y_2$, $y_3$, and $y_4$ given in table III, and with pseudo-component $y_5$ representing yields of light gases and coke. As illustrated, pseudo component $y_1$ is the heaviest (highest boiling point) component and this component will crack to lower boiling point components. For example pseudo component $y_2$ can be formed directly from pseudo-component $y_1$. Pseudo-component $y_3$ can form directly from pseudo components $y_1$ or $y_2$, and indirectly from $y_1$. Accordingly, kinetic expressions can be generalized to any number of pseudo-components, and using the small temperature range pseudo-components the modeled cracking reactions of interest are essentially first order reactions.

Catalyst deactivation is accounted for by including a decay function designated $\Phi$ in the kinetic expression. This decay function is multiplied by the intrinsic rate constant to yield the actual rate constant. The preferred form of the decay function is a second order decay to account for catalyst deactivation for all reactions and is given by the expression $$\phi = \frac{1}{1 + \alpha t_c} \quad (1)$$

where: $t_c$ is the catalyst residence time, and
$\alpha$ is the catalyst deactivation constant.

The general equation for the change in concentration of a pseudo-component i in non-dimensional form is $$\frac{dy_i}{dx} = -\frac{K_i}{S}\phi y_i + \sum_{j=1}^{i-1} \frac{K_{j,i} y_j}{S}\phi \quad (2)$$

Here, S is the weight hourly space velocity $[1/(C/Ot_c)]$ and C/O is the mass ratio of catalyst to oil.

$$\phi = \frac{1}{1+\alpha t_c x} = \frac{1}{1+\lambda x}$$

is the catalyst deactivation as given above.

x is the normalized axial length (dimensionless).

$y_i$ is the weight fraction of pseudo-component i.

$K_i$ is the rate constant for disappearance of pseudo-component i (hr.$^{-1}$), and.

$K_{ji}$ is the selectivity of a heavier pseudo-component j to the lighter pseudo component i (hr$^{-1}$).

For pseudo-component $y_1$ equation (2) becomes $$\frac{dy_1}{dx} = -\frac{K_1}{S}\phi y_1 \quad (3)$$

since $y_1$ can only disappear in a cracking reaction. The solution of this differential equation at the exit of the reactor (x=1) with the appropriate initial condition is $$y_1 = y(0)(1+\lambda)^{-K1/(\lambda S)} \quad (4)$$

$y_1$ (0) being the inlet concentration of component $y_1$.

The differential equation for pseudo-component $y_2$ is given by $$\frac{dy_2}{dx} = -\frac{K_2}{S}\phi y_2 + \frac{K_{1,2}y_1}{S}\phi \quad (5)$$

This equation is solved by dividing Equation (5) by Equation (3). On solving the resulting differential equation with the usual initial condition, we get for $y_2$.

$$y_2 = y_2(0)\left[\frac{y_1}{y_1(0)}\right]^{K_2/K_1} + \frac{K_{1,2}}{K_1-K_2}\left[y_1(0)\left[\frac{y_1}{y_1(0)}\right]^{K_2/K_1} - y_1\right] \quad (6)$$

In this equation the first term accounts for the disappearance of pseudo-component $y_2$ originally present in the feed. The second term accounts for the formation of $y_2$ from $y_1$ and its eventual disappearance on forming from $y_1$. A similar equation can be derived for pseudo-component $y_3$ which can form directly from $y_1$ or $y_2$. It can also form indirectly from $y_2$ which was formed from $y_1$. The resulting equation for $y_3$ is $$y_3 = y_3(0)\left[\frac{y_1}{y_1(0)}\right]^{K_3/K_1} + \frac{K_{1,3}}{K_1-K_3}\left[y_1(0)\left[\frac{y_1}{y_1(0)}\right]^{K_3/K_1} - y_1\right] + \quad (7)$$

$$\frac{K_{2,3}}{K_2-K_3}\left[y_2(0)\left[\frac{y_1}{y_1(0)}\right]^{K_3/K_1} - y_2\right] +$$

$$\frac{K_{1,2}K_{2,3}}{(K_1-K_3)(K_2-K_3)}\left[y_1(0)\left[\frac{y_1}{y_1(0)}\right]^{K_3/K_1} - y_1\right]$$

The first term accounts for the disappearance of $y_3$ initially present in the feed. The second and third terms account for the formation of $y_3$ from $y_1$ and $y_2$ respectively. The last term accounts for the formation of $y_3$ from $y_2$ which was formed from $y_1$. This is an indirect route to $y_3$. These kind of routes are referred to as "one stop routes". It is also possible to have a "two stop route" where a lighter pseudo-component is formed via two heavier pseudo-components. In this model it is assumed that two stop routes are highly unlikely since the reaction occurs very rapidly in a short contact time riser. "Two stop routes" are included only in the formation of light gases and coke. These routes are needed to model the overcracking of gasoline range molecules.

From Equation (7) we can write a generalized equation for all the pseudo-components lighter than $y_1$. The equation for pseudo-component N is given by the following expression $$y_N = y_N(0)\left[\frac{y_1}{y_1(0)}\right]^{K_N/K_1} + \quad (8)$$

$$\sum_{i=1}^{N-1}\frac{K_{i,N}}{K_i-K_N}\left[y_i(0)\left[\frac{y_1}{y_1(0)}\right]^{K_N/K_1} - y_i\right] +$$

$$\sum_{i=1}^{N-2}\sum_{j=i+1}^{N-1}\frac{K_{i,j}K_{j,N}}{(K_i-K_N)(K_j-K_N)}\left[y_i(0)\left[\frac{y_1}{y_1(0)}\right]^{K_N/K_1} - y_i\right]$$

As mentioned before two stop routes are considered for light gases and coke. For light gases and coke the initial concentrations are zero. Also the disappearance rate constants are negligible and assumed to be zero. The generalized equation for light gases and coke can then be written as $$y_N = \sum_{i=1}^{N-1}\frac{K_{i,N}}{K_i}[y_i(0)-y_i] + \sum_{i=1}^{N-2}\sum_{j=i+1}^{N-1}\frac{K_{i,j}K_{j,N}}{K_iK_j}[y_i(0)-y_i] + \quad (9)$$

$$\sum_{i=1}^{N-3}\sum_{j=i+1}^{N-2}\sum_{k=j+1}^{N-1}\frac{K_{i,j}K_{j,k}K_{k,N}}{K_iK_jK_k}[y_i(0)-y_i]$$

The rate constants and selectivities in the equations above are shown hereinafter as functions of feed and catalyst properties.

Feed and Catalyst Characterization

Feeds are preferably characterized using as properties total hydrogen content, aromatic carbon and hydrogen content, carbon residue, and basic nitrogen content, which are obtained with the combination of API gravity, simulated distillation and refractive index measurements. In addition, simulated distillation is preferred to characterize the initial boundary conditions for the feed. Catalyst characterization preferably uses properties including alumina content, coke on regenerated catalyst, sodium content, rare earth content, total surface area, vanadium on catalyst, and a nickel equivalent expression. This expression is defined as Ni+V/4−2 Sb in ppm.

Rate Constant Equations

Rate constants for cracking, deactivation, and product selectivity are shown below. All the rate constants have units of hr$^{-1}$. These equations are used for the broad boiling lumps described earlier (Table III), $y_1$, $y_2$, $y_3$, and $y_4$.

α=7100* exp[−1500/RT]

$K_i$'s $K_1$=29,700*exp[−8800/RT]*[(CCR/6)$^{−0.048}$* (H$_2$/12)$^{1.735}$ * (BN$_2$/750)$^{−0.049}$* (SA/140)$^{0.545}$* (1-CRC$^2$)$^{1.7}$* (RE/1.75)$^{1.041}$* (Al$_2$O$_3$/33)$^{2.377}$]

$K_2$=204,000* exp[−16,070/RT]*[(H$_2$/12)$^{1.136}$* (H$_a$/C$_a$/0.25)$^{0.155}$* (BN$_2$/750)$^{0.091}$* (EV/4000)$^{−0.081}$* (SA/140)$^{0.065}$* (1-CRC$^2$)$^{1.7}$* (Al$_2$O$_3$/33)$^{0.732}$]

$K_3$=620,000* exp[−24,115.2/RT]

$K_4$=3,300,000* exp[−32,186/RT]

$K_{ij}$'s for $y_1$, $y_2$, $y_3$, and $y_4$ $K_{12}$=4670.3* exp[−8800/RT]*[1−0.367*(CCR/6)−0.284*(BN$_2$/750) −0.933*(C$_a$/21) +1.607*(Al$_2$O$_3$/33)]

$K_{13}$=5901.7*exp[−8800/RT]*[1+0.041*(H$_a$/C$_a$/0.25)−0.085*(C$_a$/21.0) −0.195*(CCR/6.0)+0.545*(Al$_2$O$_3$/33) +0.398*(RE/1.75)−0.067*NIEQ/1660.0) −0.744*(ENa/0.4)]

$K_{14}$=6343.4 * exp[−8800/RT]*[1−0.172*(C$_a$/21.0)−0.224*(CCR/6.0) +0.685*(Al$_2$O$_3$/33)+0.699*(RE/1.75) −0.117*NIEQ/1660.0)−0.676*(ENa/0.4)]

$K_{23}$=37,878.0*exp[−16,070/RT]*[1+0.041*(H$_a$/C$_a$/0.25)−0.085*(C$_a$/21.0) +0.545*(Al$_2$O$_3$/33)+0.398*(RE/1.75) −0.067*NIEQ/1660.0)−0.744*(ENa/0.4)]

$K_{24}=87,040.5 * \exp[-16,070/RT]*[1-0.172*(C_a/21.0)+0.685*(Al_2O_3/33) +0.699*(RE/1.75)-0.117*NIEQ/1660.0)-0.676*(ENa/0.4)]$ $K_{34}=195,010.3* \exp[-24,115.2/RT]$ $K_{ij}$'s for Coke $K_{15}(coke)=5769.4 * \exp[-8800/RT]*[1+0.055*(CCR/6.0)+0.167*(H_a/C_a/0.25) +0.623*(SA/140.0)+0.325*(RE/1.75) +1.164*(Al_2O_3/33)-2.261 *(ENa/0.4)]+0.018*NIEQ/1660.0)$ $K_{25}$ (coke)$=8053.0 * \exp[-16,070/RT]*[1+1.158*(H_a/C_a/0.25)+0.428*(C_a/21.0) +0.489*(Al_2O_3/33)-0.595*(ENa/0.4) -1.389*(SA/140.0)]$ $K_{35}=114,894.6* \exp[-24,115.2/RT]$ $K_{45}=574,846.4* \exp[-32,186/RT]$ $K_{ij}$'s for $C_4$'s $K_{15}$ ($C_4$'s)$=2912.5* \exp[-8800/RT]*[1-0.268*(CCR/6.0)+0.096*(H_2/12) -0.095*(BN_2/750)+0.122*(H_a/C_a/0.25)+1.666*(SA/140.0)-0.065*NIEQ/1660.0) -1.398*(ENa/0.4)]$ $K_{25}$ ($C_4$'s)$=19,414.3*\exp[-16,070/RT]*[1+0.783*(H_2/12)-0.092*(BN_2/750) +0.147*(H_a/C_a/0.25)+0.185*(SA/140.0) -0.018*NIEQ/1660.0)-0.942*(ENa/0.4)]$ $K_{35}=157,747.2* \exp[-24,115.2/RT]$ $K_{45}=116,655.8* \exp[-32,186/RT]$ $K_{ij}$'s for $C_3$'s $K_{15}=1736.3*\exp[-8800/RT]*[1-0.043*(CCR/6.0)+0.698*(H_2/12) -0.090*(BN_2/750)+0.221 *(H_a/C_a/0.25) +1.046*(SA/140.0)-0.094*NIEQ/1660.0) -1.643*(ENa/0.4)]$ $K_{25}=8068.1*\exp[-16,070/RT]*[1+0.773*(H_2/12)-0.089*(BN_2/750) +0.074*(H_a/C_a/0.25)+0.223*(SA/140.0) -0.019*NIEQ/1660.0)-0.907*(ENa/0.4)]$ $K_{35}103,715.7*\exp[-24,115.2/RT]$ $K_{45}=1,189,337.6*\exp[-32,186 RT]$ $K_{ij}$'s for $C_2$'s $K_{15}=992.1*\exp[-8800/RT]*[1+0.826*(SA/140.0)-0.372*NIEQ/1660.0) -3.322*(ENa/0.4)+0.169*(Al_2O_3/33)+2.847*(RE/1.75)]$ $K_{25}=1007.5*\exp[-16,070/RT]$ $K_{35}=22,979.0*\exp[-24,115.2/RT]$ $K_{45}=260,993.6*\exp[-32,186/RT]$ $K_{ij}$'s for $C_1$ $K_{15}=565.9*\exp[-8800/RT]*[1+1.124*(SA/140.0)-2.784*(ENa/0.4) +0.162*(Al_2O_3/33)+1.619*(RE/1.75)]$ $K_{25}=1383.5*\exp[-16,070/RT]$ $K_{35}=16,147.3*\exp[-24,115.2/RT]$ $K_{45}=118,933.7*\exp[-32,186/RT]$ $K_{ij}$'s for $H_2$ $K_{15}=60.2*\exp[-8800/RT]*[1-15.024*(H_2/12)+6.786*(SA/140.0) +5.630*(Al_2O_3/33)+2.494*(EV/4000)]$ $K_{25}=124.0*\exp[-16,070/RT]$ $K_{35}=9936.9*\exp[-24,115.2/RT]$ $K_{45}=42,948.4*\exp[-32,186/RT]$ Light Gas Olefinicity The following equations may be used to separate $C_2$'s, $C_3$'s, and $C_4$'s into olefins and paraffins.

$C_4$ Olefinicity $C_4$ Olefinicity$=0.561*[1-0.136*(SA/140.0)+0.032*NIEQ/1660.0) +0.102*(C_a/21.0)]$ $C_3$ Olefinicity $C_3$ Olefinicity$=0.725*[1-0.071*(SA/140.0)+0.032*NIEQ/1660.0) +0.040*(C_a/21.0)-0.002*(H_2/12)]$ $C_2$ Olefinicity $C_2$ Olefinicity$=0.488*[1+0.099*(CCR/6.0)-0.044*(SA/140.0) -0.051 *(H_2/12)]$ $C_4$ Isomers The following equations may be used to separate $C_4$ olefins into $iC_4=$and other butenes and to separate $C_4$ paraffins into $iC_4$ and $nC_4$.

$iC_4$=Selectivity $iC_4$=Selectivity=0.246

$iC_4$ Selectivity $iC_4$ Selectivity$=0.709*[1-0.029*(CCR/6.0)-0.027*(SA/140.0) +0.196*(H_2/12)-0.139*(RE/1.75)]$ Rate Constants for the thirty-four Pseudo-Components Pseudo-Components (PC) for $y_1$-PC33 and PC34 and $y_2$-PC23 to PC32

The oil and catalyst chemistry was assumed to be the same as that contained for $K_1$ for PC33 and PC34, and that for K2 for PC23 to PC32, shown above. The activation energies used were different, however, as shown in Tables II and III. The pre-exponential factors and average rate constants are shown in the following table. An implicit assumption is that the amount of pseudo-component 34 cracking to 33 is zero. For PC23 to PC32, the table also shows the distribution of $K_{12}$ for each pseudo-component.

TABLE IV

| Pseudo-Component or $y_i$ | Pseudo-Component Temperature | Activation Energy, BTU/lb – mole – R | Distribution of $K_{12}$ | $K_i$ (0), hr$^{-1}$ | $K_i$ (avg), hr$^{-1}$ |
| --- | --- | --- | --- | --- | --- |
| 34 | 1025 | 8043 | — | 26,000.0 | 1578 |
| 33 | 975 | 9574 | — | 27,729.9 | 989 |
| $y_1$ | 950+ | 8800 | — | 29,700.0 | 1386 |
| 32 | 925 | 11,106 | 0 | 47,246.2 | 977 |
| 31 | 875 | 12,638 | 0 | 83,359.2 | 1014 |
| 30 | 825 | 14,170 | 0 | 120,000.0 | 857 |
| 29 | 788 | 15,304 | 0 | 140,000.0 | 675 |
| 28 | 763 | 16,070 | 0 | 160,000.0 | 591 |
| 27 | 738 | 16,836 | 0 | 180,000.0 | 510 |
| 26 | 713 | 17,602 | 0.1052 | 240,000.0 | 522 |
| 25 | 688 | 18,368 | 0.2506 | 330,000.0 | 549 |
| 24 | 663 | 19,134 | 0.4200 | 500,000.0 | 638 |
| 23 | 638 | 19,900 | 0.2242 | 480,000.0 | 470 |
| $y_2$ | 625–950 | 16,070 | 1.0 | 204,000 | 754 |
| $K_{12}$ | | | | 4670.3 | 225 |

Pseudo-Components for y3-PC13 to PC22 and y4-PC1 to PC12

The pre-exponential factors, average rate constants, and distribution for K13 and K23 are shown in Table V and for $K_{14}$, $K_{24}$, and $K_{34}$ in Table VI.

TABLE V

| Pseudo-Component or $y_i$ | Pseudo-Component Temperature | Activation Energy, BTU/lb – mole – R | Dist. of $K_{13}$ and $K_{23}$ | $K_i$ (0), hr$^{-1}$ | $K_i$ (avg), hr$^{-1}$ |
|---|---|---|---|---|---|
| $y_3$ | 375–625 | 24,115.2 | 1.0 | 620,000.0 | 144 |
| $K_{13}$ | | 8800 | | 5901.7 | 241 |
| $K_{23}$ | | 16,070 | | 37,878.0 | 151 |
| 22 | 613 | 20,666 | 0.0122 | 338,637.0 | 261 |
| 21 | 588 | 21,431 | 0.0300 | 436,801.4 | 258 |
| 20 | 563 | 22,197 | 0.0490 | 480,467.7 | 218 |
| 19 | 538 | 22,963 | 0.0707 | 485,668.8 | 169 |
| 18 | 513 | 23,729 | 0.0907 | 507,544.7 | 135 |
| 17 | 488 | 24,495 | 0.0975 | 474,190.1 | 97 |
| 16 | 463 | 25,261 | 0.1220 | 274,796.2 | 43 |
| 15 | 438 | 26,027 | 0.1520 | 103,099.1 | 12 |
| 14 | 413 | 26,793 | 0.1830 | 80,982.5 | 7 |
| 13 | 387 | 27,590 | 0.1930 | 209,665.9 | 15 |

TABLE VI

| Pseudo-Component or $y_i$ | Pseudo-Component Temperature | Activation Energy, BTU/lb – mole – R | Dist. of $K_{14}$, $K_{24}$ and $K_{34}$ | $K_i$ (0), hr$^{-1}$ | $K_i$ (avg), hr$^{-1}$ |
|---|---|---|---|---|---|
| $y_4$ | 71–375 | 32,186 | 1.0 | 3,300,000.0 | 46.7 |
| $K_{14}$ | | 8800 | | 6343.4 | 352 |
| $K_{24}$ | | 16,070 | | 87,040.5 | 458 |
| $K_{34}$ | | 24,115.2 | | 195,010.3 | 45.9 |
| 12 | 362 | 28,356 | 0.0759 | 376,856.6 | 20.2 |
| 11 | 337 | 29,122 | 0.0777 | 376,074.2 | 15.2 |
| 10 | 313 | 29,857 | 0.0771 | 566,652.8 | 18.0 |
| 9 | 287 | 30,654 | 0.0749 | 868,897.9 | 20.9 |
| 8 | 262 | 31,420 | 0.0753 | 888,071.1 | 16.4 |
| 7 | 237 | 32,186 | 0.0753 | 1,135,099.5 | 16.1 |
| 6 | 212 | 32,951 | 0.0794 | 1,964,905.1 | 21.3 |
| 5 | 187 | 33,717 | 0.0902 | 2,774,043.8 | 23.1 |
| 4 | 163 | 34,453 | 0.0914 | 3,267,215.7 | 21.1 |
| 3 | 138 | 35,219 | 0.0770 | 4,520,274.3 | 22.4 |
| 2 | 113 | 35,985 | 0.0683 | 5,704,485.2 | 21.6 |
| 1 | 71 | 37,271 | 0.1376 | 8,807,404.9 | 21.4 |

Equations for the 4-Lump Model—y1(0) is zero

The product yield model equations developed earlier are based on the broad boiling range pseudo-component, $y_1$. Thus the yields of $y_2$, $y_3$, $y_4$, coke, and all the light gases relate back to the conversion of $y_1$. The effect of C/O ratio and catalyst residence time are also contained in the equation for $y_1$. Since $y_1$ represents components boiling at 950° F. and higher, this model will not be appropriate for gas oil and lighter feeds where $y_1$ is negligible or zero. In this event, $y_2$ becomes the primary feed component.

The equations for the case of $y_1(0)$ equal to zero are shown below.

If $y_1(0)=0$ Then $$y_2 = y_2(0)*[1+\lambda] - K_2/\lambda S \quad (12)$$

$$y_3 = y_3(0)*[y_2/y_2(0)]^{K3/K2} + K_{23}/(K_2-K_3)*[y_2(0)*(y_2/y_2(0))^{K3/K2} - y_2] \quad (13)$$

$$y_4 = y_4(0)*[y_2/y_2(0)]^{K3/K2} + K_{24}/(K_2-K_4)*[y_2(0)*(y_2/y_2(0))^{K4/K2} - y_2]$$

$$+ K_{34}/(K_3-K_2)*[y_3(0)*(y_2/y_2(0))^{K4/K2} - y_3]$$

$$+ [K_{23}K_{34}/((K_3-K_4))]*[y_2(0)*(y_2/y_2(0))^{K4/K2} - y_2] \quad (14)$$

$$y_5 = K_{25}/K_2*[y_2(0)-y_2] + K_{35}/K_3*[y_3(0)-y_3] + K_{45}/K_4*[y_4(0)-y_4]$$

$$+ [K_{23}K_{35}/(K_2-K_3)*[y_2(0)-y_2] + [K_{24}K_{45}/(K_2-K_4)]*[y_2(0)-y_2]$$

$$+ [K_{34}K_{45}/(K_3-K_4)*[y_3(0)-y_3]$$

Computer Simulation

Figure 3:
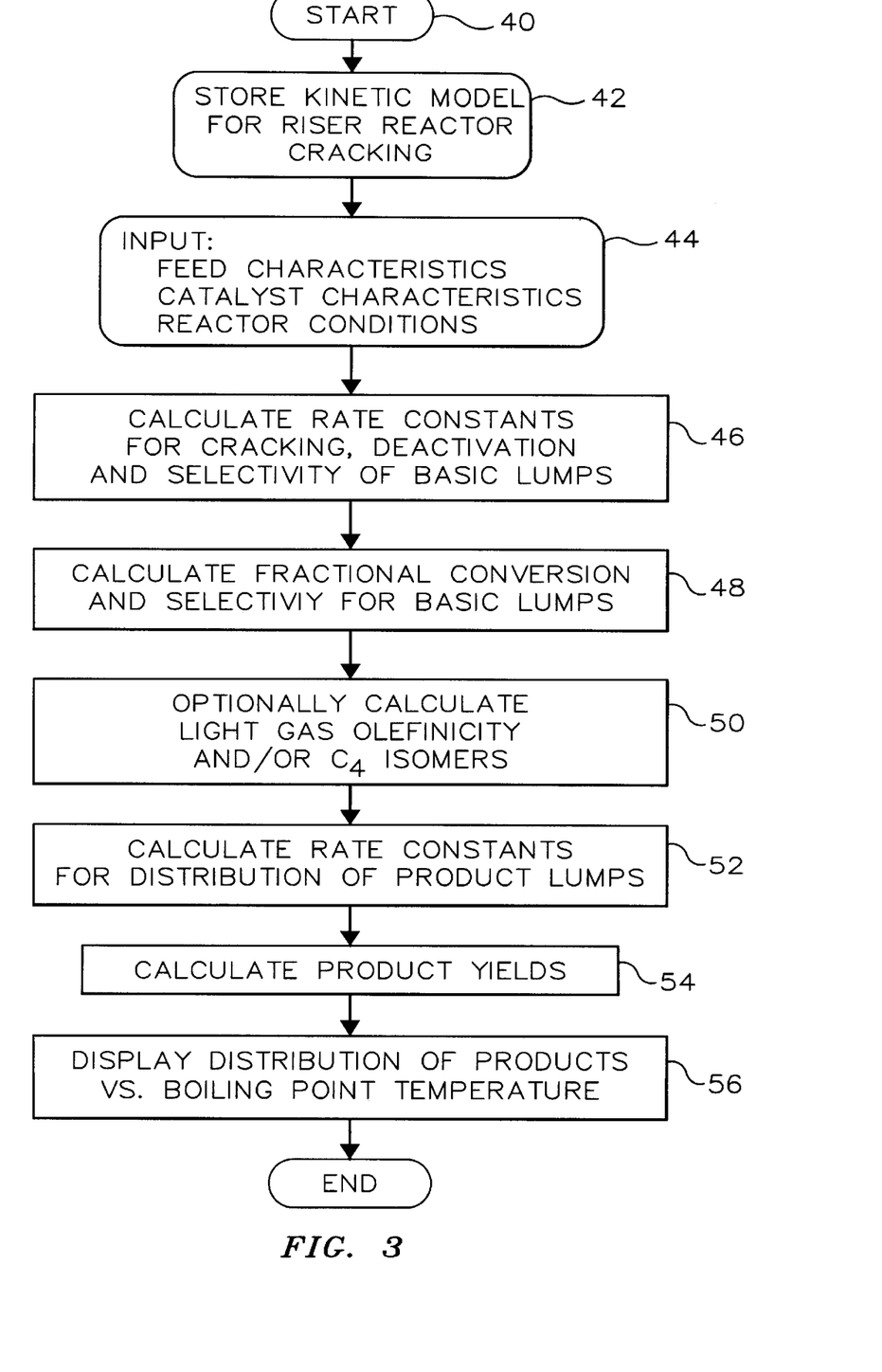
FIG. 3 is a computer flow diagram illustrating the riser reactor model algorithm for simulating riser cracker of oil according to the present invention.

For simulating a reaction on a digital computer, it is only necessary to provide the computer with necessary data and to program the computer with a routine that describes what is happening in the reactor. Referring now to FIG. 3, there is illustrated a flow sheet of a computer routine which defines a sequence of computer operating steps for predicting the product yields resulting from the fluidized catalytic cracking of residual oils. The prediction is based on the solution of equations (4)–(8) and the rate constant equations, which are stored in the routine along with coefficients and constants shown in the various Tables. The solutions reveal the variation of product yields versus boiling point temperature.

The routine is made operational at a start step 40, as illustrated in FIG. 3 when called by a mainline program (not illustrated) but which will typically be a heat balance routine between the reactor and regenerator of the FCC process. Referring to flow block 42, the kinetic model is stored in the computer using any suitable means so that the kinetic model is available for processing data. Initial data and intermediate data including values for oil and catalyst properties and operating data indicated in block 44 are input into the routine. Values for S and $t_c$ must also be specified.

Figure 4:
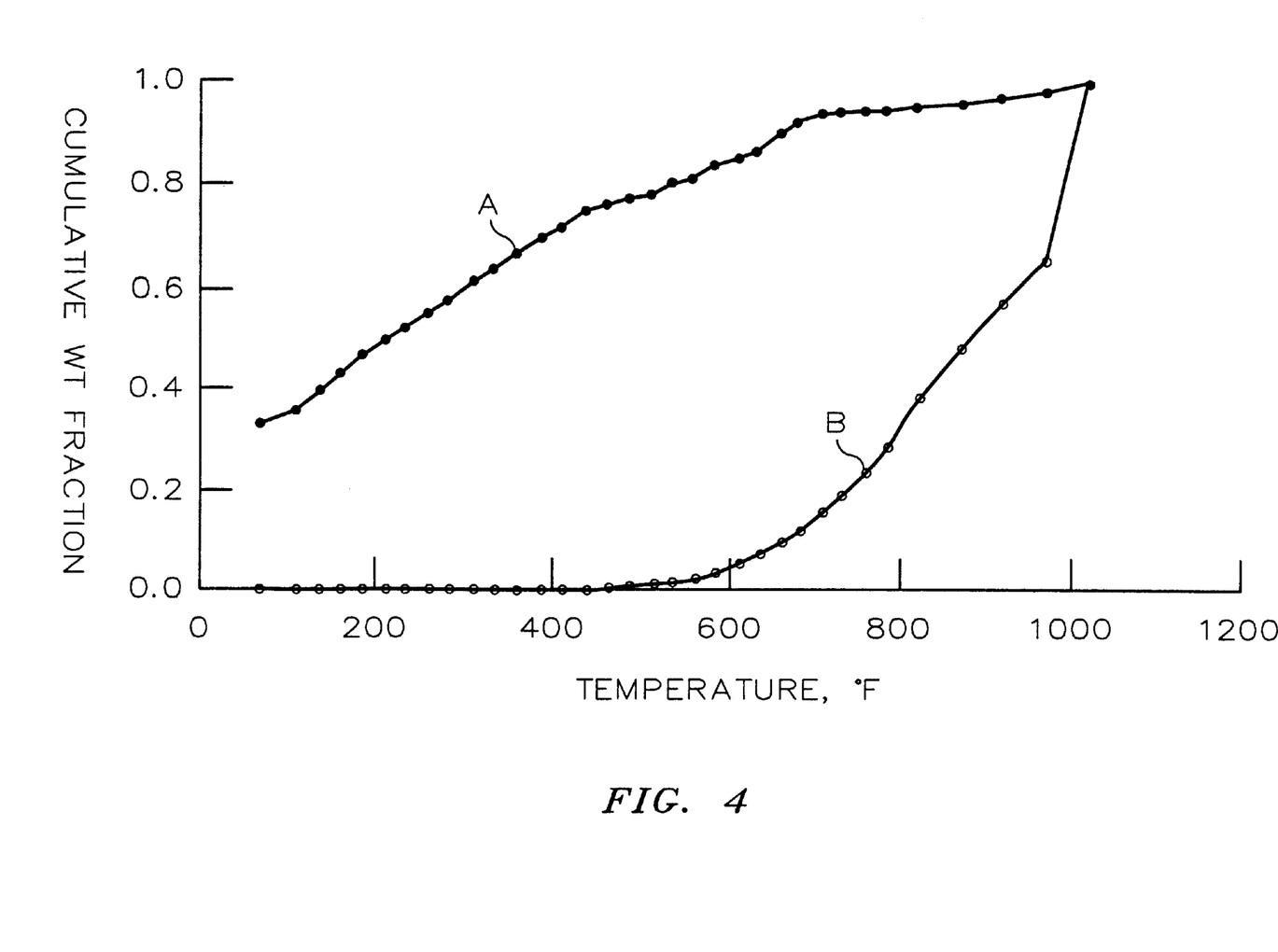
FIGS. 4–5 are graphic illustrations of reaction product distribution predicted by computer simulation.
Figure 5:
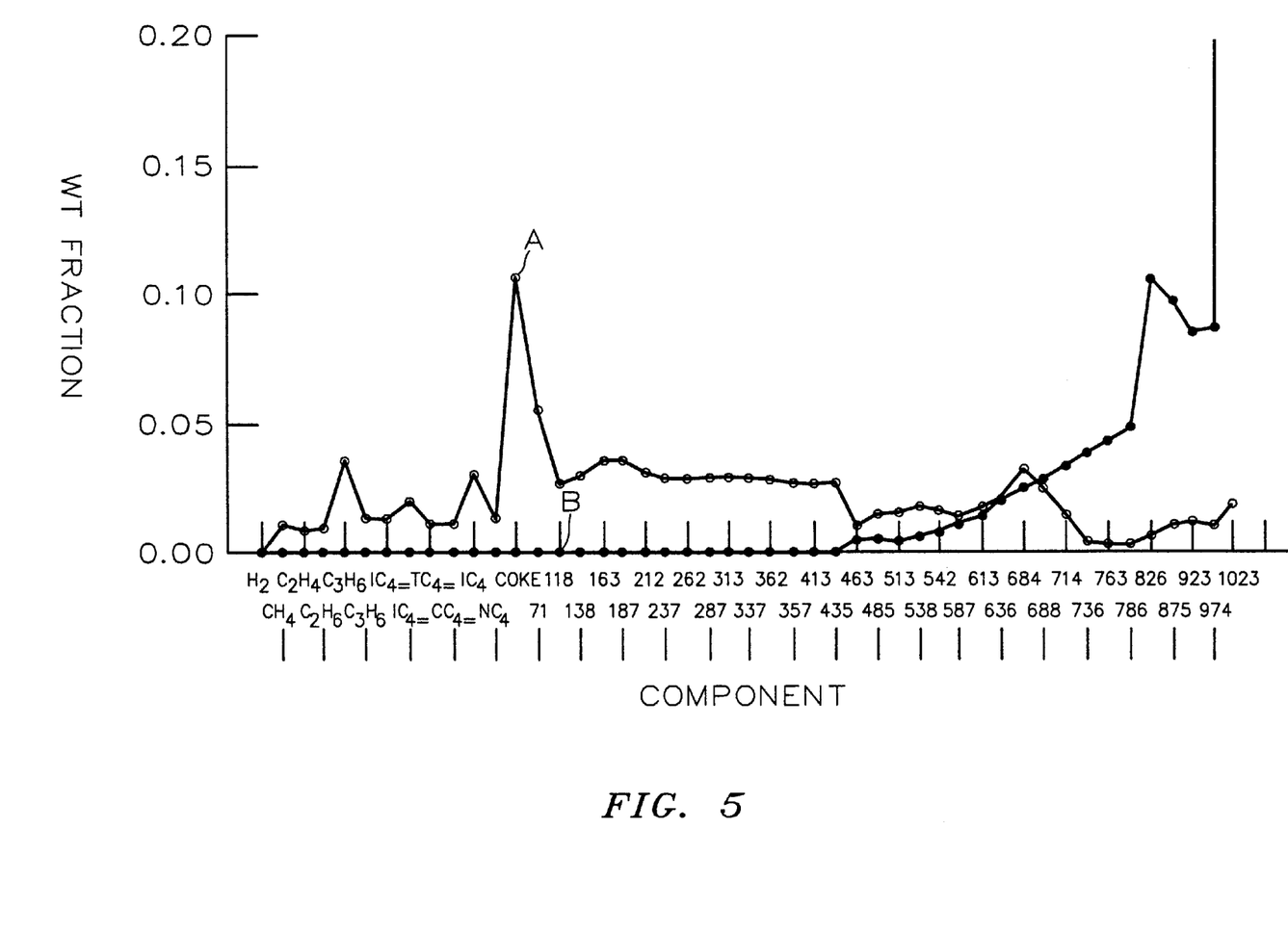
Figure 6:
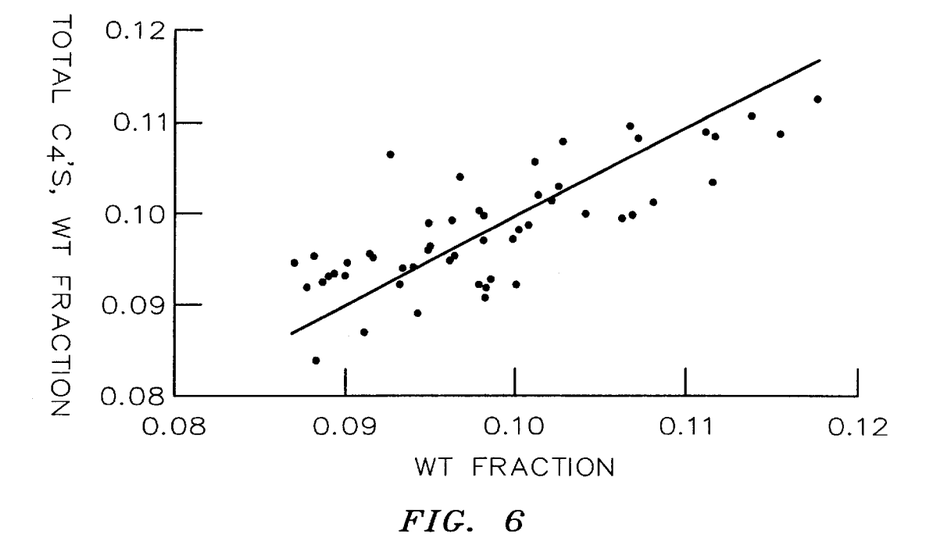
FIGS. 6–7 are graphic illustrations comparing computer simulation predictions of product yields with actual commercial plant data.
Figure 7:
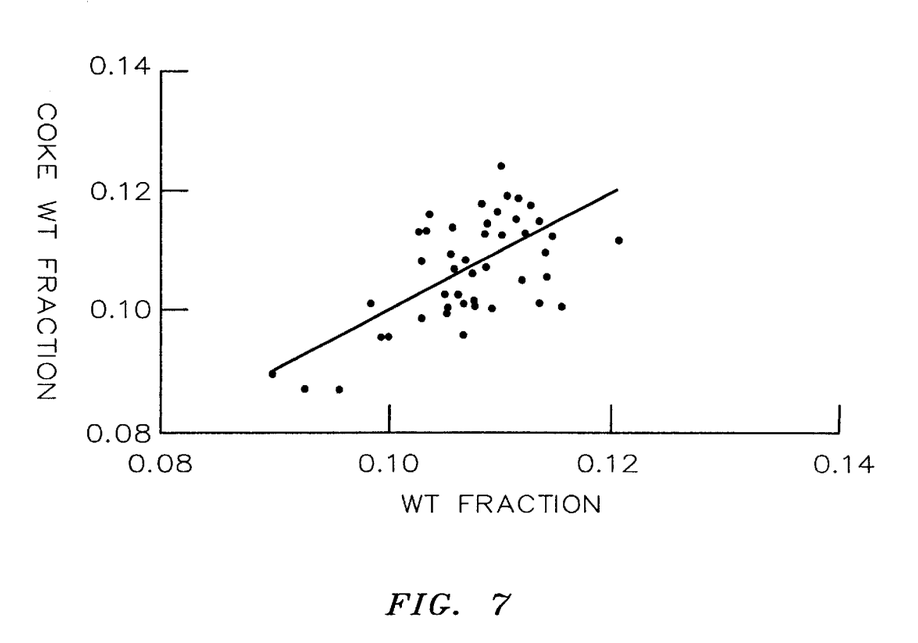

In calculation step shown in block 46, the routine calculates the rate constants as functions of feed and catalyst properties, temperature, and reactor configuration input in the previous step according to equations developed for the basic lumps. Next the routine proceeds to the calculation step in block 48 where the weight fraction of the basic lumps is computed according to equations (4)–(8). The calculation step in block 50 involves equations, which are functions of catalyst surface area, nickel equivalent aromatic carbon and hydrogen content, that may be used to separate $C_2$, $C_3$ and $C_4$ components into olefins and paraffins. Further in block 50, an equation which is a function of carbon residue, surface area, hydrogen content and rare earth content may be used to separate $C_4$ olefins into $iC_4$ olefins and other butenes, and to separate $C_4$ paraffins into normal and iso paraffins. Proceeding to the calculation step in block 52, rate constants for distribution of the thirty-four narrow boiling range product lumps included in the basic lumps are calculated based on the same oil and catalyst chemistry used for calculating for basic lumps. The activation energies used, however, are different and are illustrated in tables IV through VI. Product yields are then calculated in block 54, and displays such as illustrated in FIGS. 4–5 are generated in step 56 of the routine. Curve A of FIGS. 4 and 5 illustrates the distribution of $C_5$ products versus boiling point and curve B illustrates the distribution of fresh feed plus recycle.

Accordingly there has been described a system and method for modeling and simulating a catalytic cracking reaction carried out in a riser reactor in which the feed is characterized with a boiling point distribution and chemical properties. The computer program simulating this process is based on a relatively large number of pseudo components of the products that yields an essentially continuous distribution of products as a function of boiling point.

While the invention has been described in terms of the presently preferred embodiment, reasonable variations and modifications are possible by those skilled in the art and such variations and modifications are within the scope of the described invention and this appended claims.

GLOSSARY

Notation $Al_2O_3$=alumina content (a matrix activity marker), wt %
$BN_2$=basic nitrogen, ppm
C/O=catalyst to oil ratio
$C_a$=aromatic carbon, wt %
CCR=carbon residue, wt %
CRC=coke on regenerated catalyst, wt %
ENa=sodium on equilibrium catalyst, wt %
EV=vanadium on equilibrium catalyst, ppm
$H_2$=hydrogen content, wt %
$H_a/C_a$=aromatic hydrogen to carbon ratio
$K_i$=rate constant of disappearance of pseudo-component i, $hr^{-1}$
$K_i(0)$=pre-exponential of disappearance of pseudo-component i, $hr^{-1}$
$K_{j,i}$=selectivity of a heavier pseudo-component j to the lighter pseudo component i, $hr^{-1}$
$K_{j,i}(0)$=pre-exponential of a heavier pseudo-component j to the lighter pseudo component i, $hr^{-1}$
NIEQ=nickel equivalent, ppm (Ni+V/4−2 Sb)
RE is rare earth content, wt %
S is weight hourly space velocity $[1/(C/Ot_c)]$
SA is catalyst surface, $m^2/g$
$t_c$ is catalyst contact time, hr
x is dimensionless axial length
$y_i$ is weight fraction of pseudo-component i
$y_1$=950° F.$^+$PC1+PC2
$y_2$=625–950° F.=PC3 to PC12
$y_3$=375–625° F.=PC13 to PC22
$y_4$=71–375° F.=PC23 to PC34
$y_5$=$H_2$ to $nC_4$ and coke (separate equations for all gases)

Greek Letters $\alpha$=catalyst deactivation constant, $hr^{-1}$
$\lambda = \alpha * tc$
$\Phi$=catalyst deactivation, dimensionless That which is claimed is:

1. A method for mathematically modeling a catalytic cracking reaction wherein a feed stream containing a multiplicity of complex hydrocarbon molecules having various boiling points is contacted with an active catalyst in a riser reactor under catalytic cracking conversion conditions to produce a desired reaction product of lower molecular weight, said method comprising the following steps;

(a) lumping said multiplicity of complex hydrocarbons according to boiling-range into a plurality of model lumps, said model lumps including:
 i) a plurality of product lumps comprising small fixed boiling-range pseudo-components for describing yields of said reaction product;
 ii) a plurality of basic lumps comprising larger fixed boiling-range pseudo-components each comprising (groupings of said plurality of product lumps for describing feed conversion and selectivity, and wherein the number of lumps in said plurality of basic lumps is less than the number of lumps in said plurality of product lumps;

(b) defining a conversion reaction network for said plurality of basic lumps, wherein reaction paths in said conversion reaction network flow from heavier to lighter components;

(c) constructing a first plurality of chemical kinetic cracking equations in terms of said plurality of basic lumps for each step in said conversion reaction network based on a generalized equation for change in concentration for each of said plurality of basic lumps, and wherein said generalized equation integrates catalyst decay with chemical kinetics;

(d) constructing a second plurality of chemical kinetic cracking equations in terms of said plurality of product lumps for each step in said conversion reaction network based on said generalized equation for change in concentration for each of said plurality of product lumps and for distribution of each of said plurality of basic lumps into the product lumps corresponding to each of said plurality of basic lumps; wherein said second plurality of chemical kinetic cracking equations are dependent on the basic lump concentrations determined using said first plurality of chemical kinetic cracking equations; and (e) wherein the combination of said first and second plurality of chemical kinetic cracking equations comprise a kinetic model for the riser reactor cracking of said multiplicity of complex hydrocarbon molecules.

2. A method in accordance with claim 1, wherein said plurality of product lumps comprises thirty-four pseudo-components covering a boiling-point temperature range of from about 40° F. to about 1500° F., and wherein said plurality of basic lumps comprises five pseudo-components covering the same overall boiling point temperature range.

3. A method in accordance with claim 2, wherein said plurality of product lumps additionally includes eleven hydrocarbon components characterized as pure components and coke.

4. A method in accordance with claim 1, wherein said kinetic model includes reaction rate constants expressed as functions of oil and catalyst properties, temperatures and reactor configuration.

5. A method in accordance with claim 4, wherein said oil properties include;
   i) carbon residue:
   ii) total nitrogen;
   iii) basic nitrogen;
   iv) hydrogen (CHNS);
   v) aromatic hydrogen (NMR); and
   vi) aromatic carbon.

6. A method in accordance with claim 4, wherein said catalyst properties include;
   i) alumina content;
   ii) coke on regenerated catalyst;
   iii) sodium content;
   iv) rare earth content;
   v) total surface area;
   vi) vanadium on catalyst; and
   vii) a nickel equivalent expressed as : Ni+V/4–2Sb.

7. A method according to claim 1, wherein said generalized equation in non-dimensional form for change in concentration of said plurality of lumps comprises;

$$\frac{dy_i}{dx} = -\frac{K_i}{S}\phi y_1 + \sum_{i=1}^{i-1} \frac{K_{j,i} y_j}{S}\phi$$

where: $y_i$ is the weight fraction of pseudo-component i
$\Phi$ is the catalyst deactivation function;
x is the normalized axial length of the reactor (dimensionless)
S is the weight hourly space velocity;
$K_i$ is the rate constant for disappearance of pseudo-component i; and
$K_{ji}$ is the selectivity of a heavier pseudo-component j to the lighter pseudo-component i.

8. A method in accordance with claim 1, wherein said feed stream comprises a residual oil feed stream.

9. A computer implemented method for simulating a catalytic cracking reaction wherein a feed stream containing a multiplicity of complex hydrocarbon molecules having various boiling points is contacted with an active catalyst in a riser reactor under catalytic cracking conversion conditions to produce a desired reaction product of lower molecular weight, said method comprising the following steps:
   (a) providing said computer with a kinetic model for simulating said cracking reaction, said kinetic model including at least;
      i) a plurality of product lumps comprising small fixed boiling-range pseudo-components for describing yields of said reaction product;
      ii) a plurality of basic lumps comprising larger fixed boiling-range pseudo-components each comprising groupings of said plurality of product lumps for describing feed conversion and selectivity and wherein the number of lumps in said plurality of basic lumps is less than the number of lumps in said plurality of product lumps;
      (iii) a conversion reaction network for said plurality of basic lumps, wherein reaction paths in said conversion reaction network flow from heavier to lighter components;
      (iv) a first plurality of chemical kinetic cracking equations in terms of said plurality of basic lumps for each step in said reaction network based on a generalized equation for change in concentration for each of said plurality of basic lumps; and wherein said generalized equation integrates catalyst decay with chemical kinetics;
      (v) a second plurality of chemical kinetic cracking equations in terms of said plurality of product lumps for each step in said conversion reaction network based on said generalized equation for change in concentration for each of said plurality of product lumps and for distribution of each of said plurality of basic lumps into the product lumps corresponding to each of said plurality of basic lumps; wherein said second plurality of chemical kinetic cracking equations are dependent on the basic lump concentrations determined using said first plurality of chemical kinetic cracking equations;
   (b) providing said computer with initial data including at least: feed characteristics, catalyst characteristics, and reactor conditions;
   (c) repeatedly calculating values for the following conditions according to said kinetic model:
      i) said reaction rate constants at riser reactor temperature;
      ii) fractional conversion of the feed;
      iii) distribution of said product lumps within said basic lumps; and
      iv) yields of lower molecular weight products; and
   (d) displaying the distribution of cracked products in terms of boiling point temperature.

10. A method in accordance with claim 9, wherein said plurality of product lumps comprises thirty-four pseudo-components covering a boiling-point temperature range of from about 40° F. to about 1500° F., and wherein said plurality of basic lumps comprises five pseudo-components covering the same overall boiling point temperature range.

11. A method in accordance with claim 10, wherein said plurality of product lumps additionally includes eleven hydrocarbon components characterized as pure components and coke.

12. A method in accordance with claim 9, wherein said kinetic model includes reaction rate constants expressed as functions of oil and catalyst properties, temperatures and reactor configuration.

13. A method in accordance with claim 12, wherein said oil properties include;
   i) carbon residue;
   ii) total nitrogen;
   iii) basic nitrogen;
   iv) hydrogen (CHNS);
   v) aromatic hydrogen (NMR); and
   vi) aromatic carbon.

14. A method in accordance with claim 12, wherein said catalyst properties include:
   i) alumina content;
   ii) coke on regenerated catalyst;
   iii) sodium content;
   iv) rare earth content;
   v) total surface area;
   vi) vanadium on catalyst; and
   vii) a nickel equivalent expressed as: Ni+V/4–2Sb.

15. A method according to claim 9, wherein said generalized equation in non-dimensional form for change in concentration of said plurality of lumps comprises;

$$\frac{dY_1}{dx} = -\frac{Ki}{S}\phi y_1 + \sum_{j=1}^{i-1} \frac{K_{j,i} y_j}{S}\phi$$

where: $y_i$ is the weight fraction of pseudo-component i,
$\Phi$ is the catalyst deactivation function;
x is the normalized axial length of the reactor (dimensionless)

S is the weight hourly space velocity;

$K_i$ is the rate constant for disappearance of pseudo-component i; and $K_{ji}$ is the selectivity of a heavier pseudo-component j to the lighter pseudo-component i.

16. A method in accordance with claim 9, wherein said feed stream comprises a residual oil feed stream.

17. Apparatus for simulating a catalytic cracking reaction wherein a feed stream containing a multiplicity of complex hydrocarbon molecules having various boiling points is contacted with an active catalyst in a riser reactor under catalytic cracking conversion conditions to produce a desired reaction, said apparatus comprising;

a computer programmed to perform method steps comprising:
  (a) storing a kinetic model in said computer for simulating said cracking reaction, said kinetic model including at least;
    i) a plurality of product lumps comprising small fixed boiling-range pseudo-components for describing yields of said reaction product;
    ii) a plurality of basic lumps comprising larger fixed boiling-range pseudo-components each comprising groupings of said plurality of product lumps for describing feed conversion and selectivity and wherein the number of lumps in said plurality of basic lumps is less than the number of lumps in said plurality of product lumps;
    (iii) a conversion reaction network for said plurality of basic lumps, wherein reaction paths in said conversion reaction network flow from heavier to lighter components;
    (iv) a first plurality of chemical kinetic cracking equations in terms of said plurality of basic lumps for each step in said reaction network based on a generalized equation for change in concentration for each of said plurality of basic lumps; and wherein said generalized equation integrates catalyst decay with chemical kinetics;
    (v) a second plurality of chemical kinetic cracking equations in terms of said plurality of product lumps for each step in said conversion reaction network based on said generalized equation for change in concentration for each of said plurality of product lumps and for distribution of each of said plurality of basic lumps into the product lumps corresponding to each of said plurality of basic lumps; wherein said second plurality of chemical kinetic cracking equations are dependent on the basic lump concentrations determined using said first plurality of chemical kinetic cracking equations;
  (b) providing said computer with initial data including at least: feed characteristics, catalyst characteristics, and reactor conditions;
  (c) repeatedly calculating values for the following conditions according to said kinetic model:
    i) said reaction rate constants at riser reactor temperature;
    ii) fractional conversion of the feed;
    iii) distribution of said product lumps within said basic lumps; and
    iv) yields of lower molecular weight products; and
  (d) displaying the distribution of cracked products in terms of boiling point temperature.

18. A method in accordance with claim 17, wherein said plurality of product lumps comprises thirty-four pseudo-components covering a boiling-point temperature range of from about 40° F. to about 1500° F., and wherein said plurality of basic lumps comprises five pseudo-components covering the same overall boiling point temperature range.

19. A method in accordance with claim 18, wherein said plurality of product lumps additionally includes eleven hydrocarbon components characterized as pure components and coke.

20. A method in accordance with claim 17, wherein said kinetic model includes reaction rate constants expressed as functions of oil and catalyst properties, temperatures and reactor configuration.

21. A program storage device, readable by a computer, tangibly embodying a program of instructions executable by said computer to perform method steps for simulating a catalytic cracking reaction wherein a feed stream containing a multiplicity of complex hydrocarbon molecules having various boiling points is contacted with an active catalyst in a riser reactor under catalytic cracking conversion conditions to produce a desired reaction product of lower molecular weight, said method steps comprising;

(a) storing a kinetic model in said computer for simulating said cracking reaction, said kinetic model including at least;
    i) a plurality of product lumps comprising small fixed boiling-range pseudo-components for describing yields of said reaction product;
    ii) a plurality of basic lumps comprising larger fixed boiling-range pseudo-components each comprising groupings of said plurality of product lumps for describing feed conversion and selectivity, and wherein the number of lumps in said plurality of basic lumps is less than the number of lumps in said plurality of product lumps;
    (iii) a conversion reaction network for said plurality of basic lumps, wherein reaction paths in said conversion reaction network flow from heavier to lighter components;
    (iv) a first plurality of chemical kinetic cracking equations in terms of said plurality of basic lumps for each step in said reaction network based on a generalized equation for change in concentration for each of said plurality of basic lumps; and wherein said generalized equation integrates catalyst decay with chemical kinetics;
    (v) a second plurality of chemical kinetic cracking equations in terms of said plurality of product lumps for each step in said conversion reaction network based on said generalized equation for chance in concentration for each of said plurality of product lumps and for distribution of each of said plurality of basic lumps into the product lumps corresponding to each of said plurality of basic lumps; wherein said second plurality of chemical kinetic cracking equations are dependent on the basic lump concentrations determined using said first plurality of chemical kinetic cracking equations;
  (b) repeatedly calculating values for the following conditions according to said kinetic model:
    i) said reaction rate constants at riser reactor temperature;
    ii) fractional conversion of the feed;
    iii) distribution of said product lumps within said basic lumps;
    iv) yields of lower molecular weight products; and
  (c) displaying the distribution of cracked products in terms of boiling point temperature.

* * * * *

UNITED STATES PATENT AND TRADEMARK OFFICE
CERTIFICATE OF CORRECTION

PATENT NO. : 6,212,488 B1 Page 1 of 1
DATED : April 3, 2001
INVENTOR(S) : Paul F. Meier, Dhananjay B. Ghonasgi, and Michael D. Wardinsky It is certified that error appears in the above-identified patent and that said Letters Patent is hereby corrected as shown below:

Column 18, claim 21,
Line 48, please delete "chance" and insert therefor -- change --.

Signed and Sealed this

Fifth Day of March, 2002

*Attest:*

*Attesting Officer*

JAMES E. ROGAN
*Director of the United States Patent and Trademark Office*